US007166731B2

(12) United States Patent
Park et al.

(10) Patent No.: US 7,166,731 B2
(45) Date of Patent: Jan. 23, 2007

(54) METHOD OF PREPARING FULVENE COMPOUNDS AND METHOD OF PREPARING ANSA-METALLOCENE COMPOUNDS USING THE COMPOUNDS

(75) Inventors: Young Whan Park, Daejeon (KR); Hyosun Lee, Daejon (KR); Sung Don Hong, Daejeon (KR); Kwang Ho Song, Daejeon (KR); Boong Goon Jeong, Daejeon (KR); Dae Woo Nam, Daejeon (KR); Hye Young Jung, Goyang (KR); Bun Yeoul Lee, Suwon (KR); Young Chul Won, Chuncheon (KR)

(73) Assignee: LG Chem. Ltd., Seoul (KR)

( * ) Notice: Subject to any disclaimer, the term of this patent is extended or adjusted under 35 U.S.C. 154(b) by 199 days.

(21) Appl. No.: 10/962,482

(22) Filed: Oct. 13, 2004

(65) Prior Publication Data

US 2005/0080296 A1 Apr. 14, 2005

(30) Foreign Application Priority Data

Oct. 14, 2003 (KR) ...................... 10-2003-0071444

(51) Int. Cl.
*C07F 17/00* (2006.01)
*C07C 13/00* (2006.01)
*C07C 49/00* (2006.01)
(52) U.S. Cl. ..................... 556/53; 568/379; 568/667; 568/669; 585/23
(58) Field of Classification Search .................. 556/53; 568/379, 667, 669; 585/23
See application file for complete search history.

(56) References Cited

FOREIGN PATENT DOCUMENTS

| KR | P1998-0025280 A | 6/1998 |
|---|---|---|
| KR | 1020040019717 A | 6/2004 |
| KR | 1020040019718 A | 6/2004 |
| WO | WO 2005035470 A1 * | 4/2005 |

OTHER PUBLICATIONS

Won et al., Synthesis, No. 7, pp. 1052-1056 (published on the Web Feb. 4, 2004).*
"ansa-Metallocene derivatives", XVII. Racemic and meso diastereomers of group IV metallocene derivatives with symmetrically substituted, . . . , Journal of Organometallic Chemistry, 369 (1989) 359-370, Elsevier Sequoia S.A., Lausanne—Printed in The Netherlands; by Helga Wiesenfeldt, Annette Reinmuth, Elke Barsties, Kaspar Evertz and Hans-Herbert Brintzinger.
"ansa-Metallocene derivatives", XVI. Chiral titanocene and zirconocene derivatives with symmetrically substituted, . . . ,Journal of Organometallic Chemistry, 369 (1989) 343-357, Elsevier Sequoia S.A., Lausanne—Printed in The Netherlands; by Stephan Gutmann, Peter Burger, Hans-Ulrich Hund, Josef Hofmann and Hans-Herbert Brintzinger.
Synthesis of [2,2'-Methylenebis (1,3-dimethylcyclopentadienyl) zirconium Dichloride and Its Reactivity in Ethylene-Norbornene Copolymerization by Bun Yeoul Lee, Young Heui Kim, Young Chul Won, Jin Wook Han, Won Hyuk Suh, In Su Lee, Young Keun Chung and Kwang Ho Song, Department of Molecular Science and Technology, Ajou University, Korea, received Oct. 15, 2001.
Synthesis, molecular structure, and polymerization reactivity of ethylenebis (1,3-dimethylcyclopentadienyl) zirconium dichloride by Bun Yeoul Lee, Young Heui Kim, Young Chul Won, Chang Bo Shim, Dong Mok Shin and Young Keun Chung, Department of Molecular Science and technology, Ajou Univeristy, Korea, received Apr. 22, 2002.
General Synthetic Routes to Chiral, Ethylene-Bridged ansa-Titanocene Dichlorides by S. Collins and Nicholas J. Taylor, Guelph Waterloo Centre for Graduate Work in Chemistry, University of Waterloo, Ontario, Canada, received Feb. 22, 1990.
Fulvene having substituents only on 1-,4-, and 6-positions: a key intermediate for novel ansa-metallocene complexes by Young Chul Won, Heon Yong Kwon, Bun Yeoul Lee and Young-Whan Park, Department of Molecular Science and Technology, Ajou University, received Apr. 3, 2003.
Direct α-Iodination of Cycloalkenones by Carl R. Johnson, Joseph P. Adams, Mastthew P. Braun and C.B.W. Senanayake, Department of Chemistry, Wayne State University; and Peter M. Wovkulich and Milan R. usokovic, Roche Research Center, hoffmann-La Roche, Inc., pp. 917-918, received Nov. 13, 1991.

* cited by examiner

*Primary Examiner*—Porfirio Nazario-Gonzalez
(74) *Attorney, Agent, or Firm*—Birch, Stewart, Kolasch & Birch, LLP

(57) ABSTRACT

There are provided a method of simply preparing a 1,4,6-substituted, 1,4-substituted, 1,6-substituted, or 1-substituted fulvene compound, the intermediates of the fulvene compound, and a method of preparing an ansa-metallocene compound in which two cyclopentadienyl ligands are bridged by one carbon and there are substituents only at positions adjacent to the bridging point of a cyclopentadienyl ligand, using the fulvene compound.

18 Claims, No Drawings

METHOD OF PREPARING FULVENE COMPOUNDS AND METHOD OF PREPARING ANSA-METALLOCENE COMPOUNDS USING THE COMPOUNDS

BACKGROUND OF THE INVENTION

This application claims the priority of Korean Patent Application No. 2003-71444, filed on Oct. 14, 2003, in the Korean Intellectual Property Office, the disclosure of which is incorporated herein in its entirety by reference.

1. Field of the Invention

The present invention relates to a simple method of preparing 1,4,6-substituted, 1,4-substituted, 1,6-substituted, or 1-substituted fulvene compounds, and a novel intermediate derived from the method. Also, the present invention relates to a method of preparing an ansa-metallocene compound using the fulvene compound and the novel intermediate. Particularly, the present invention relates to a simple, mass-producible method of preparing an ansa-metallocene compound having substituents only at positions adjacent to the bridging point of cyclopentadienyl ligand(s).

2. Description of the Related Art

The ansa-metallocene compound can be vitally used as an olefin polymerisation catalyst.

The ansa-metallocene catalyst having substituents only at positions adjacent to the bridging point was proposed by the present inventor. The present inventor demonstrated that an excellent performance is obtained when a monomer having high steric hindrance, such as a norbornene, is copolymerised with an ethylene, due to low steric hindrance at reaction point, by the ansa-metallocene catalyst. See Korean Patent Application No. 10-98-12658; *Organometallics,* 2002, 21, 1500–1503 and *J. Organomet. Chem.,* 2002, 660, 161–166. However, as shown in Reaction Scheme I below, the preparation method is not easy one, and thus has a problem in mass production. Particularly, the synthesis of 1,4-pentadiyne, a starting material of the preparation process of the ansa-metallocene catalyst, is not commercially available. A serial procedure consisting of incorporating a substituent via Pauson-Khand reaction by using the starting material and performing the reverse Diels-Alder reaction is performed at a stringent condition, such as high temperature or high pressure, has many reaction steps, and needs separating-purifying operation by chromatography method, etc. for the intermediates of each reaction steps. Further, the Reaction Scheme has disadvantage that the process use excessive amounts of methyllithium which is dangerous and expensive. Accordingly, the catalyst cannot be easily prepared in commercially significant amounts by Reaction Scheme I below, due to such reasons.

Reaction Scheme I

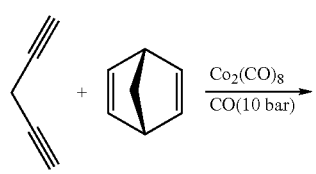

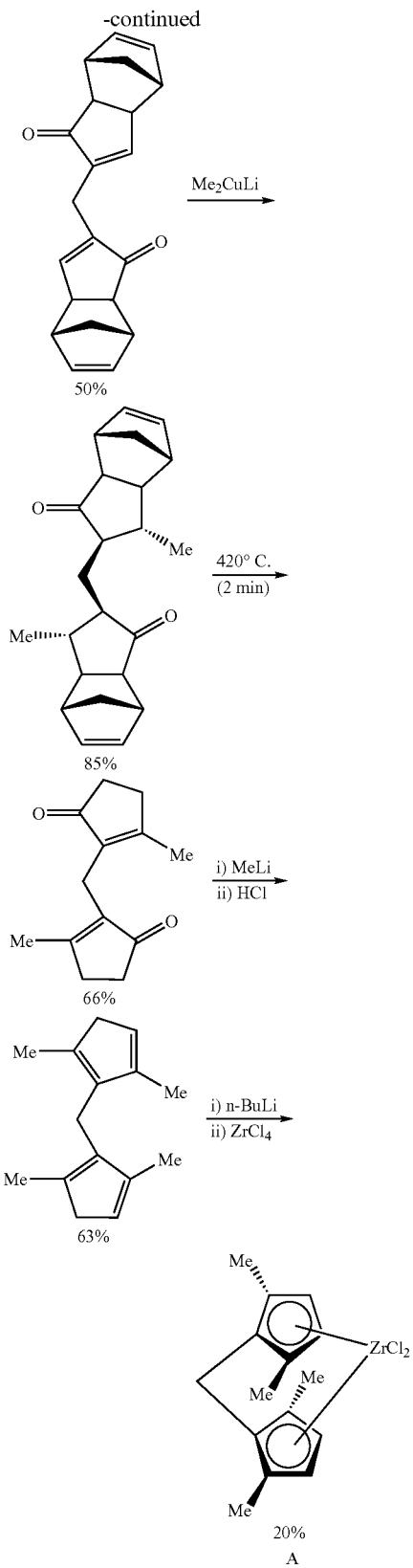

For the method of more easily preparing the metallocene catalysts having a substituent at positions adjacent to the bridging point, the method of preparing 1,4,6-substituted, 1,4-substituted, 1,6-substituted, or 1-substituted fulvene compound according to Reaction Scheme II below (Korean Patent Application No. 10-2002-51425) and the method of preparing the metallocene catalyst according to Reaction Scheme III by employing the former method (Korean Patent Application No. 10-2002-51426) have been filed previously.

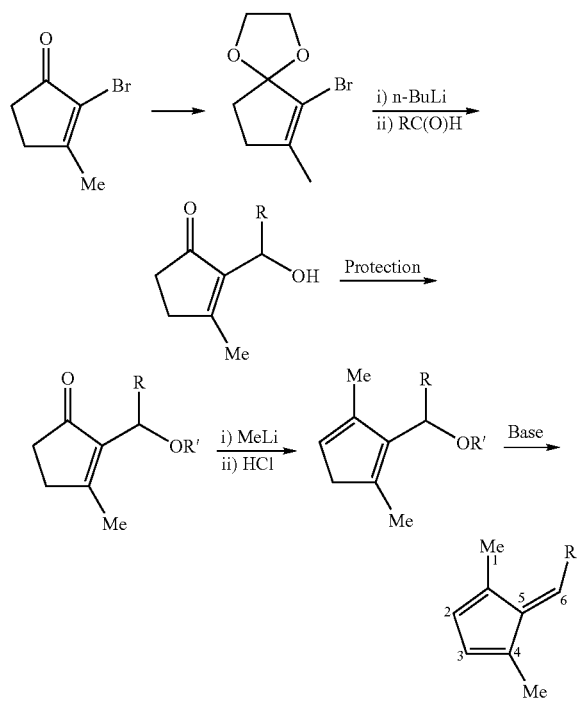

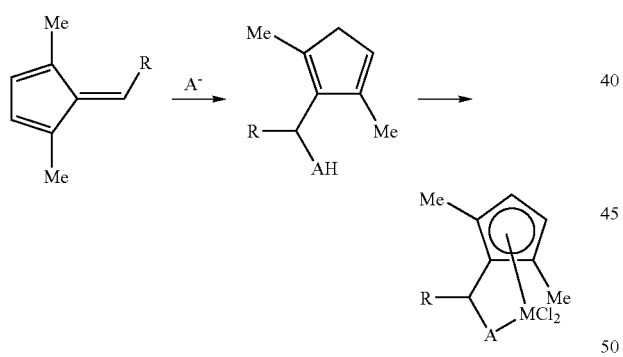

However, the preparation steps are also too complicated for this case. Particularly, these include protecting-deprotecting steps which are not preferable for mass production such as protection of a ketone to a ketal, organometallic reaction, and then deprotection of the ketal. Further, even though various metallocene catalysts can be prepared by the Reaction Scheme III from the new fulvene prepared by the Reaction Scheme II, the compound A of the Reaction Scheme I cannot be prepared. According to the patent applications, a novel metallocene compound is prepared by preparing a ligand through nucleophilic attack of a cyclopentadienyl, an indenyl, a fluorenyl, an amido, a phosphino anion or their derivatives to a fulvene, and then attaching a metal to the ligand. Reaction of 1,3-dimethylcyclopentadienyl anion is with a 1,4-dimethylfulvene, for the purpose of preparation of the compound is A of the Reaction Scheme I, affords a compound having methyl groups at 1- and 4-positions according to the rightward direction in the Reaction Scheme IV below due to the steric hindrance effect, instead of the desired ligand by the reaction of leftward direction of the scheme.

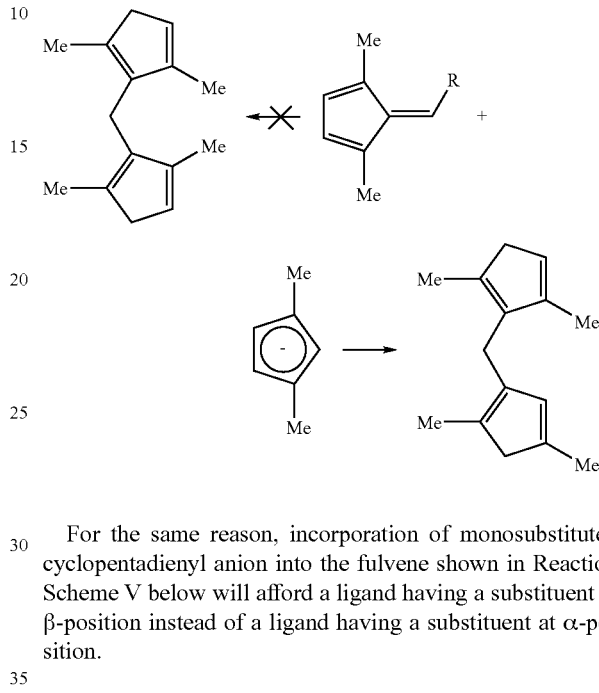

For the same reason, incorporation of monosubstituted cyclopentadienyl anion into the fulvene shown in Reaction Scheme V below will afford a ligand having a substituent at β-position instead of a ligand having a substituent at α-position.

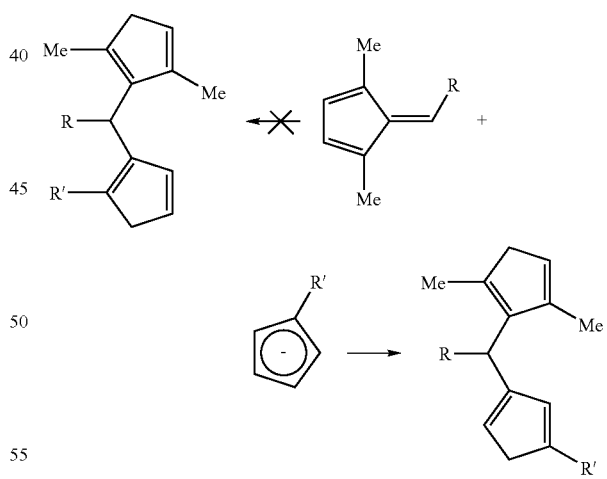

The present invention provides the methods capable of overcoming two problems described above. The present invention provides a method of preparing 1,4,6-substituted, 1,4-substituted, 1,6-substituted, or 1-substituted fulvene compound in short steps without protecting-deprotecting procedures. Further, the present invention provides a method of easily preparing a metallocene compound having a substituent only at positions adjacent to a bridging point as shown in the Reaction Schemes IV and V.

SUMMARY OF THE INVENTION

The present invention provides a method of preparing a 1,4,6-substituted, 1,4-substituted, 1,6-substituted, or 1-substituted fulvene compound.

According to an aspect of the present invention, there is provided an intermediate compound in preparing a metallocene compound having substituents only at positions adjacent to a bridging point, and a method of preparing the same.

According to another aspect of the present invention, there is provided a method of preparing an ansa-metallocene compound in which two cyclopentadienyl ligands are bridged by one carbon and there are substituents only at positions adjacent to the bridging point of a cyclopentadienyl ligand, using the fulvene compound and the novel intermediate.

DETAILED DESCRIPTION OF THE INVENTION

The present invention will be described in more detail by describing embodiments thereof.

The present invention provides a method of preparing a 1,4,6-substituted, 1,4-substituted, 1,6-substituted, or 1-substituted fulvene compound comprising a) reacting Formula I below with a compound of Formula IIa or IIb below to prepare a compound of Formula III below;

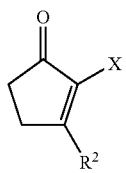
(I)

$R^1$—Li  (IIa)

$R^1$—MgX  (IIb)

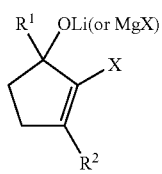
(III)

b) lithiating the compound of the Formula III, and then reacting the resulting lithium salt with an electrophile of Formula IV below to prepare a compound of Formula V below;

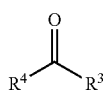
(IV)

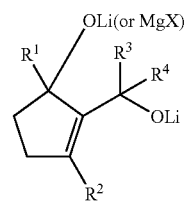
(V)

c) reacting more than one equivalent of the compound of the Formula V with a compound of Formula VI below to prepare an ether, and then dehydrating with an acid catalyst to prepare a compound of Formula VII below; and $R^5$—Y  (VI)

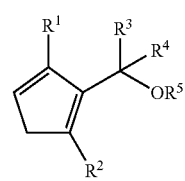
(VII)

d) adding a base to the compound of the Formula VII to prepare a fulvene compound of Formula VIII (VIII)

In the Formulae I~VIII, $R^1$, $R^2$, $R^3$ and $R^4$ are each independently or simultaneously a hydrogen atom; a $C_1$–$C_{20}$ alkyl or aryl comprising optionally an oxygen atom; or a $C_1$–$C_{20}$ alkenyl, alkylaryl or arylalkyl, and $R^1$ is not a hydrogen atom, and $R^3$ and $R^4$ can be connected together by an alkylidene radical comprising a $C_1$–$C_{20}$ alkyl or aryl radical to form a ring;

X is a halogen atom;

$R^5$ is a $C_1$–$C_{20}$ alkyl, alkenyl, alkylaryl, or a radical of Group XIV metal substituted with an arylalkyl, an aryl, an alkoxyalkyl or a hydrocarbyl;

Y is a leaving group formed by a nucleophilic substitution reaction.

The present invention provides a novel precursor (Formula VII) of the fulvene compound from which a 1,4,6-substituted, 1,4-substituted, 1,6-substituted, or 1-substituted fulvene compound (Formula VIII) can be easily obtained by a chemical treatment. The compound of the Formula VII or the compound of the Formula VIII are prepared via the compound of the Formula III.

Thus, the present invention provides a compound of Formula VII below and a method of preparing the same

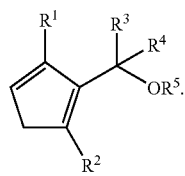
(VII)

Specifically, the method of preparing the compound of the Formula VII comprises a) reacting Formula I below with a compound of Formula IIa or IIb below to prepare a compound of Formula III below;

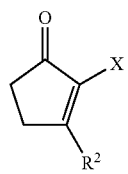
(I)

$R^1$—Li (IIa)

$R^1$—MgX (IIb)

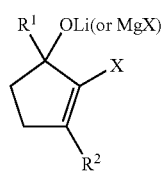
(III)

b) lithiating the compound of the Formula III, and then reacting the resulting lithium salt with an electrophile of Formula IV below to prepare a compound of Formula V below; and

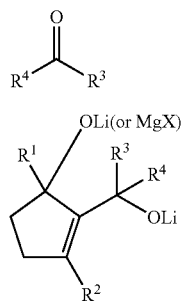
(IV)

(V)

c) reacting more than one equivalent of the compound of the Formula V with a compound of Formula VI below to prepare an ether, and then dehydrating with an acid catalyst to prepare a compound of Formula VII below $R^5$—Y (VI)

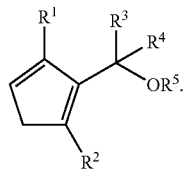
(VII)

In the Formula I~VII, $R^1$, $R^2$, $R^3$, $R^4$, $R^5$, X and Y are the same as defined above.

The 1,4,6-substituted, 1,4-substituted, 1,6-substituted, or 1-substituted fulvene compound (Formula VIII) can be formed by adding a base to the compound of the Formula VII.

The specific examples of the compound of the Formula I used in the step a) include 2-bromo-2-cyclopentene-1-one, 2-bromo-3-methyl-2-cyclopentene-1-one, 2-bromo-3-ethyl-2-cyclopentene-1-one, 2-iodo-2-cyclopentene-1-one, 2-iodo-3-methyl-2-cyclopentene-1-one, 2-iodo-3-ethyl-2-cyclopentene-1-one, 2-bromo-3-propyl-2-cyclopentene-1-one, 2-bromo-3-phenyl-2-cyclopentene-1-one, 2-iodo-3-phenyl-2-cyclopentene-1-one, 2-bromo-3-butyl-2-cyclopentene-1-one, 2-bromo-3-tolyl-2-cyclopentene-1-one, 2-bromo-3-ethenyl-2-cyclopentene-1-one, 2-bromo-3-prophenyl-2-cyclopentene-1-one, 2-bromo-3-cumyl-2-cyclopentene-1-one, etc. Of these compounds, 2-bromo-2-cyclopentene-1-one, 2-bromo-3-methyl-2-cyclopentene-1-one and 2-iodo-3-methyl-2-cyclopentene-1-one, etc. are preferable.

The specific examples of the compound of the Formula IV used as the reactant in the step b) include acetone, formaldehyde, acetaldehyde, benzaldehyde, benzophenone, methylethylketone, butyraldehyde, propionaldehyde, etc. Of these compounds, formaldehyde, acetaldehyde and benzaldehyde, etc. are preferable.

The examples of the leaving group formed by the nucleophilic substitution reaction in the compound of the Formula VI used as a reactant in the step c) include chlorine, bromine, iodide, methoxymethyl, trifluorosulfonate, and paratoluenesulfonate, etc.

Further, the present invention provides an intermediate compound of Formula IX in preparing a metallocene compound having a substituent only at positions adjacent to a bridging point, and a method of preparing the same. The compound of the Formula IX can be prepared by reacting the compound of the Formula III below with the compound of the Formula VI below.

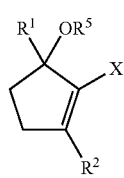
(IX)

-continued

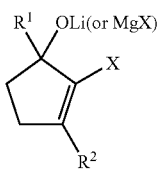
(III)

$R^5$—Y  (VI)

In the Formulae, $R^1$, $R^2$, $R^5$ and X are the same as defined in the Formulae I~VIII.

Further, the present invention provides a method of preparing the compound of Formula VII from the compound of the Formula IX, and a method of preparing the fulvene compound of the Formula VIII from the compound of the Formula VII.

The method of preparing the compound of the Formula VII from the compound of the Formula IX comprises a) lithiating the compound of the Formula IX, or converting the compound with a Grignard reagent, and then reacting the resulting organometallic compound with an electrophile of Formula IV below to prepare a compound of Formula X below; and

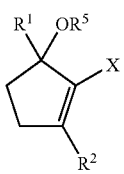
(IX)

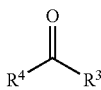
(IV)

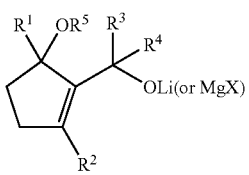
(X)

b) reacting more than one equivalent of the compound of the Formula X with a compound of Formula VI below to prepare an ether, and then dehydrating with an acid catalyst to prepare a compound of Formula VII below $R^5$—Y  (VI)

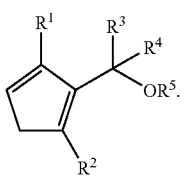
(VII)

Further, the present invention provides a method of preparing a compound of Formula XI below, which is a precursor of a metallocene compound having substituents only at the α-positions with respect to the bridging point of a 5-membered cyclopentadienyl ring, comprising lithiating the compound of the Formula III or the compound of the Formula IX, or converting the compounds with a Grignard reagent, and then reacting the resulting organometallic compounds with the compound of the Formula VII below, and then treating with an acid:

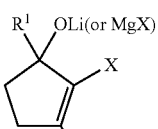
(III)

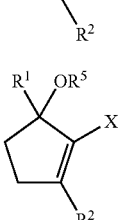
(IX)

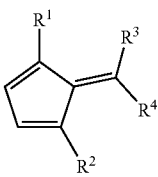
(VIII)

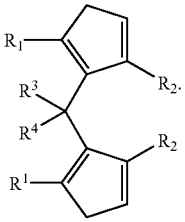
(XI)

The method of preparing a compound of Formula XII below, which is a metallocene compound having substituents only at the α-positions with respect to the bridging point of a 5-membered cyclopentadienyl ring, from the compound of the Formula XI can follow the method described in various literatures regarding the preparation of a metallocene compound in ansa-form from a compound in which two 5-membered cyclopentadienyl rings are bridged:

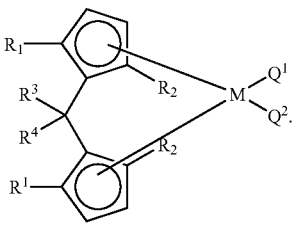
(XII)

In the Formula XI and XII, each of $R^1$, $R^2$, $R^3$ and $R^4$ is independently or simultaneously a hydrogen atom; a $C_1$–$C_{20}$ alkyl or aryl comprising optionally an oxygen atom; or a $C_1$–$C_{20}$ alkenyl, alkylaryl or arylalkyl, and $R^1$ is not a hydrogen atom, and $R^3$ and $R^4$ can be connected together by an alkylidene radical comprising a $C_1$–$C_{20}$ alkyl or aryl radical to form a ring.

In the $MQ^1Q^2$, $Q^1$ and $Q^2$ are each independently or simultaneously a halogen atom; a $C_1$–$C_{20}$ alkyl, alkenyl, alkylaryl or arylalkyl; an aryl; a substituted or unsubstituted $C_1$–$C_{20}$ alkylidene; a substituted or unsubstituted amido group; a $C_1$–$C_{20}$ alkylalkoxy; or an arylalkoxy; and M is a Group IV metal.

The method of preparing the compound of the Formula XII from the compound of the Formula XI includes a method that the compound of the Formula XI is treated with a strong base, such as KH, Mg and alkyl lithium, to form a divalent anion, and then reacted with a metal compound comprising at least two halogen atoms per a metal element, thereby obtaining the compound of the Formula XII. See H. Wiesenfeldt et al, *J. Organomet. Chem.*, 369 359 (1989), S. Gutmann et al, *J. Organomet. Chem.*, 369 343 (1989), and S. Collins et al, *Organometallics*, 9 2695 (1990). Another method includes a method that the divalent anion formed by treating the compound of the Formula XI with a strong base is reacted with a Group XIV metalloid organic metal compound comprising at least one halogen element to substitute each 5-membered ring with a metalloid element, and then reacted with a metal compound comprising at least two halogen atoms per a metal element, thereby obtaining the compound of the Formula XII. See Bunyeoul Lee et al, *J. Organomet. Chem.*, 660 161 (2002). Still another method includes a method that the compound of the Formula XI is used as such without treating with a base, and reacted with a metal amido compound, as described in U.S. Pat. No. 5,998,643. According to the most preferable method of these methods, the compound of the Formula XI is treated with 2 equivalents of n-butyl lithium to dehydrogenate each 5-membered cyclopentadienyl ring, thereby forming a divalent anion, and by the reaction of the divalent anion with a metal halide compound, etc., a bridged metallocene compound comprising a cyclopentadienyl group containing one carbon at bridge position and a substituent only at α position can be prepared.

Hereinafter, the present invention is described in more detail. The present invention provides a method of preparing 1,4,6-substituted, 1,4-substituted, 1,6-substituted, or 1-substituted fulvene compounds. Further, the present invention relates to a method of preparing an ansa-metallocene compound in which two cyclopentadienyl ligands are bridged by one carbon and there is a substituent only at positions adjacent to the bridging point of a cyclopentadienyl ligand, using the fulvene compound.

A method of preparing the fulvene compound of the Formula VIII follows the Reaction Scheme VI below.

Reaction Scheme VI

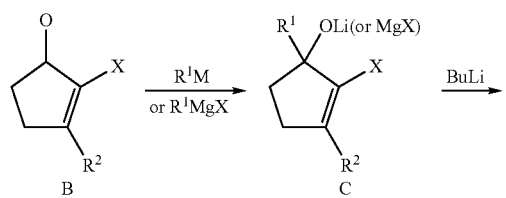

-continued

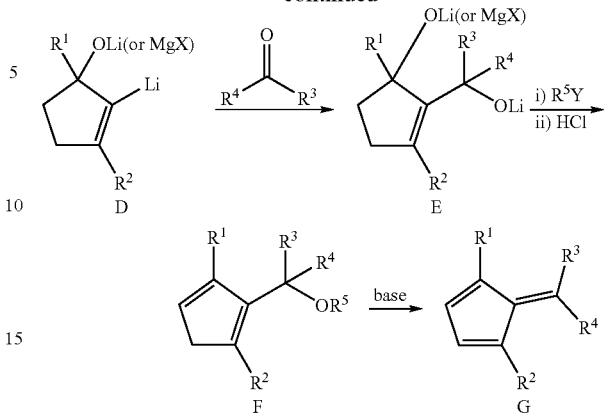

In the Reaction Scheme VI, $R^1$–$R^5$ are the same as defined above. In the starting material compound B (Formula I), X is a halogen atom including I, Br or Cl, preferably Br or I. The compound that X is Br is mass-producible by previously known methods (*J. Organomet. Chem.*, 677(2003), 133). The compound that X is I is also mass-producible by previously known methods (*Tetrahedron Lett.*, 33(1992), 917). In the Reaction Scheme VI, nucleophilic attack of the organometallic compounds of the Formulae IIa or IIb to the compound B where X is Br affords an anionic compound C (Formula II) of a tertiary alcohol, and subsequently alkyl lithium is added at a low temperature in the identical reactor to prepare the lithium salt (compound D). The lithium salt is reacted with an electrophile of the Formula IV to obtain a dilithium salt (compound E). Herein, the form of $R^3$ and $R^4$ can be defined by the structure of the electrophile. When the compound, such as an alkyl halide or an alkyl sulfonate, according to the Formula VI is added in the same equivalent to the compound E (Formula V), the oxo anion attached on the carbon, to which $R^3$ and $R^4$ are also attached, is converted to an ether group. When two equivalents of the compound according to the Formula VI are used, the oxo anion attached on the carbon substituted with $R^1$, is also converted to an ether group. At this reaction step, the oxo anions attached on the carbons substituted with $R^1$ need not be necessarily converted to ethers, however, it is preferable that the oxo anions are all converted to ethers. Finally, when an acid is added, the OH or alkoxy group attached on the carbon substituted with $R^1$ is eliminated as water or an alcohol with the hydrogen atom attached on an adjacent carbon, and thus a double bond is formed, thereby obtaining the compound F (Formula VII) of the Reaction Scheme VI. The compound can be used after purification by the vacuum distillation or chromatography, or can be also used in next reaction without purification. If the compound F (Formula VII) is treated with a base in various solvents, desired fulvene compound G (Formula VIII) can be obtained.

Preferably, the compound F can be obtained by sequentially adding reactants in one reactor without isolating and purifying intermediate compounds C, D and E from the compound B. However, the procedure of the isolation and purification of the intermediates must not limit the present invention. For example, the method of preparing the compound D by adding water to the compound C to form an alcohol, purifying it, and then adding the excessive butyl lithium, or the method of preparing the compound F by adding water to the compound E to convert to an alcohol, isolating and purifying it, protecting the alcohol in various ways, and then treating with an acid, or the method of preparing the compound F by adding water to the compound E to convert to an alcohol, dehydrating by treating with an acid to obtain a cyclopentadienyl compound, and then protecting the rest of the alcohol, etc. also pertain to the scope of the present invention. Further, if desired, the compounds C, D and E can be also used after purification with various ways.

The compound according to the Formula IX, which can be used as an intermediate in preparing the ansa-metallocene compound in which two cyclopentadienyl ligands are bridged by one carbon and there are substituents only at positions adjacent to the bridging point of two cyclopentadienyl ligands, can be prepared by Reaction Scheme VII below. That is, when the compound of the Formula VI is reacted with the compound of the Formula III, which is an intermediate in preparing a fulvene, the compound H (Formula IX) of the Reaction Scheme VII below is obtained. Further, the compound H (Formula IX) can be also obtained by adding water to the compound C (Formula III), isolating and purifying it to obtain an alcohol compound, and then protecting the alcohol functional group. The method of protecting an alcohol group by converting to an ether compound such that the alcohol group can be stable under subsequent organometallic reaction condition include well-known organic synthetic methods, such as the method of substituting the hydrogen atom of an alcohol with an alkyl group, the method of substituting the hydrogen atom of an alcohol with an alkoxyalkyl group, or the method of protecting by insertion to a cycloalkene compound. Such protecting method of an alcohol is well described in "Protective Groups in Organic Synthesis", 3$^{rd}$ Ed. (T. W. Green 1999).

Reaction Scheme VII

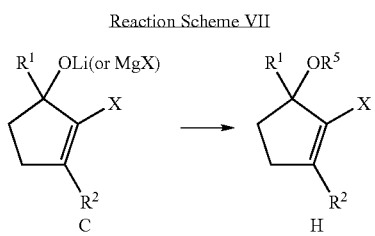

The fulvene compound according to the Formula VIII can be also prepared by using the compound H (Formula IX) of the Reaction Scheme VII. In the method, the fulvene compound can be prepared via the same reaction step by using the compound H (Formula IX) of the Reaction Scheme VII instead of the compound C. When the compound H (Formula IX) is used instead of the compound C (Formula III), lithium metal can be used instead of expensive butyl lithium to generate lithium salt, or the compound H can be converted with the Grignard reagent instead of making lithium salt, and then the resulting product can be reacted with the compound of the Formula IV to prepare the intermediate compound according to the Formula VII. Then, subsequent reaction can be proceeded to obtain desired object.

The ansa-metallocene compound in which two cyclopentadienyl ligands are bridged by one carbon and there are substituents only at positions adjacent to the bridging point of two cyclopentadienyl ligands, can be prepared by Reaction Scheme VIII below. The ligand compound I (Formula XI) is obtained by reacting the fulvene compound G (Formula VIII) of the Reaction Scheme VI with a material produced by making lithium salt of the compound D (Formula II) prepared in the Reaction Scheme VI or the compound H (Formula IX) of the Reaction Scheme VII or converting them with the Grignard reagent, and then treating the resulting compound with an acid. A metallocene compound J (Formula XII) can be prepared from the compound I (Formula XI) by various known methods.

Reaction Scheme VIII

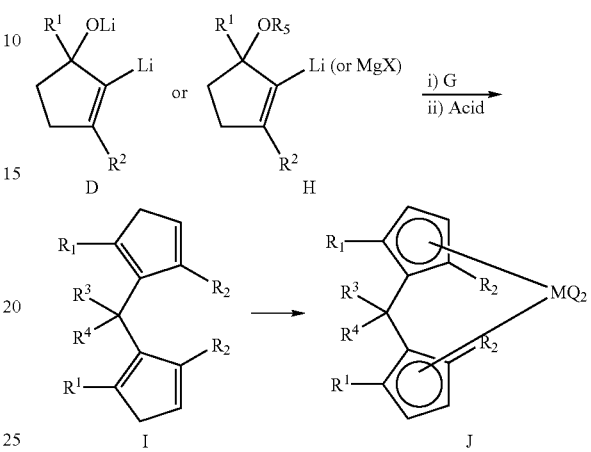

The present invention will be described in greater detail with reference to the following examples. The following examples are for illustrative purposes and are not intended to limit the scope of the invention.

EXAMPLES

The organic reagents and solvents were purchased from the Aldrich Company and Merck Company, and used after purification by a standard method. The reproducibility of an experiment was elevated by blocking the contact with air and moisture in all steps of preparation. The spectrum was obtained to verify the structure of a compound by using 400 MHz nuclear magnetic resonance spectrometer (NMR).

Example 1

Preparation of a
2-methoxymethyl-1,3-dimethyl-cyclopenta-1,3-diene
[Formula VII (R$^1$, R$^2$=CH$_3$; R$^3$, R$^4$=H)]

121.7 ml of 1.1 equivalents of methyl lithium solution was slowly added to 300 ml of tetrahydrofuran solution in which 29 g (166 mmol) of 2-bromo-3-methyl-2-cyclopentene-1-one [Formula I (R$^2$=CH$_3$, X=Br)] compound are dissolved at −78° C. nitrogen state, and then the mixture was reacted for 2 hours. 195.3 ml of 2.0 equivalents of tertiary butyl lithium solution was slowly added at the same temperature, and then the mixture was reacted for 2 hours. 3 equivalents of paraformaldehyde and the catalytic amount of paratoluenesulfonic anhydride were reacted at 100° C., and then the resulting formaldehyde gas was introduced in a reaction flask. After the completion of introducing the formaldehyde gas, the solvent was removed under reduced pressure while slowly elevating the temperature to a room temperature. After the removal of the solvent, 250 ml of dimethylformamide was injected into the reaction vessel using a cannula. 2 equivalents of methyl iodide were added thereto and the mixture was reacted for 15 hours. Then one equivalent of sodium hydride and the same equivalents of methyl iodide were added, and the mixture was reacted for a day. After the completion of the reaction, 300 ml of water and 300 ml of a sodium chloride solution were added and the mixture was extracted with 600 ml of hexane and once again with 200 ml of hexane. An organic layer was washed three times with 200 ml of a sodium chloride solution and the solvent was removed with a rotatory evaporator, and then 300 ml of ethyl acetate was added. 200 ml of 2N HCl solution was added to the extracted organic layer, and the resulting mixture was vigorously shaken for 2 minutes. Water layer was removed and the organic layer was neutralized with 200 ml of a saturated sodium bicarbonate solution. Isolated organic layer was treated with magnesium sulfate to remove water, and then vacuum-distillated to give 14.2 g of white 2-methoxymethyl-1,3-dimethyl-cyclopenta-1,3-diene. Yield: 62%.

$^1$H NMR (CDCl$_3$): δ 5.83 (s, 1H, CH), 4.15 (s, 2H, OCH$_2$), 3.33 (s, 3H, OCH$_3$), 2.85 (s, 2H, CH$_2$), 2.05 (s, 3H, CH$_3$), 1.99 (s, 3H, CH$_3$) ppm. $^{13}$C{$^1$H} NMR (CDCl$_3$): δ 142.95, 142.81, 123.65, 65.73, 57.72, 44.36, 14.13, 13.92 ppm.

Example 2

Preparation of 1,4-demethyl Fulvene [Formula VIII (R$^1$, R$^2$=CH$_3$; R$^3$, R$^4$=H)]

4.74 g (34.3 mmol) of the 2-methoxymethyl- 1,3-dimethyl-cyclopenta-1,3-diene prepared in the example 1 were dissolved in 30 mf of pentane under nitrogen atmosphere, and one equivalent of sodium hydride was added at –20° C., the mixture was reacted for 3 hours while slowly elevating the temperature. Then, the reactant was only filtered, without separate purification, to obtain a pentane solution, and the solution was used in next reaction. By isolating a portion of the product, 1,4-dimethyl fulvene compound could be confirmed.

$^1$H NMR (C$_6$D$_6$): δ 5.95 (d, J=1.2 Hz, 2H, CH), 5.41(t, J=1.2 Hz, 2H, CH$_2$), 1.89 (d, J=1.2 Hz, 6H, CH$_3$) ppm. $^{13}$C{$^1$H} NMR (C$_6$D$_6$): δ 154.51, 131.17, 128.98, 114.71, 12.44 ppm.

Example 3

Preparation of 2-bromo-3-methoxy-1,3-dimethyl-cyclopentene [Formula IX (R$^1$, R$^2$, R$^5$=CH$_3$)]

152 ml (0.228 mol) of methyl lithium solution was placed in 1 L flask at nitrogen atmosphere, and then the solvent was removed under reduced pressure. Then 0.10 L of tetrahydrofuran was injected, and then a solution in which 40 g (0.228 mol) of 2-bromo-3-methyl-2-cyclopentene-1-one [Formula I (R$^2$=CH$_3$, X=Br)] compound are dissolved in 0.1 L of tetrahydrofuran at –78° C., was injected, and then the mixture was stirred for 1 hour. After 1 hour, the solvent was removed under reduced pressure, then 0.2 L of dimethylformamide was added, and then one equivalent of methyl iodide was added with stirring. After reaction at 40° C. for 2 hours, one equivalent of sodium hydride was added and the same equivalent of methyl iodide was added, and the mixture was reacted at 40° C. for 15 hours. After the completion of the reaction, 400 ml of water was added and the organic layer extracted with 600 ml of hexane was washed three times with 200 ml of a sodium chloride solution, then the organic layer was dried with a sodium carbonate solution, and then the solvent was removed with a rotary evaporator, and then the vacuum distillation was preformed at 500 mTorr, 50° C. to give 32.7 g of 2-bromo-3-methoxy-1,3-dimethyl-cyclopentene compound. Yield: 79%.

$^1$H NMR (CDCl$_3$): δ 3.11 (s, 3H, OCH$_3$), 2.42–2.24 (m, 2H, CH$_2$), 2.18 (ddd, J=14.0, 4.0, 9.2 Hz, 1H, CH$_2$), 1.92 (ddd, J=14.4, 5.6, 9.2 Hz, 1H, CH$_2$), 1.82 (s, 3H, CH$_3$) ppm. $^{13}$C{$^1$H} NMR (CDCl$_3$): δ 141.49, 121.78, 88.35, 50.30, 34.83, 31.98, 26.34, 16.37 ppm.

Example 4

Preparation of 2,2'-methylenebis(1,3-dimethyl-1,3-cyclopentadien) [Formula XI (R$^1$, R$^2$=CH$_3$; R$^3$, R$^4$=H)]

One equivalent of n-butyl lithium was added to a solution in which 7.038 g (34.3 mmol) of 2-bromo-3-methoxy-1,3-dimethyl-cyclopentene compound prepared in the example 3 was dissolved in 38 ml of ether at –25° C. nitrogen atmosphere. When white solid was precipitated, the temperature was elevated to 10° C. and the reaction was continued for further 10 minutes. The temperature was lowered to –25° C. and the fulvene compound prepared in the example 2 was added. Completion of reaction is determined by the development of yellow color of the reaction mixture. 50 ml of water was added to the reaction mixture and the solvent was removed using the rotatory evaporator. 50 ml of 2N HCl solution was added to the organic layer extracted with 50 ml of ethyl acetate, and the resulting mixture was vigorously shaked for 2 minutes. Water layer was removed by layer separation and the organic layer was neutralized with 50 ml of a saturated sodium bicarbonate solution. Isolated organic layer was dried over magnesium sulfate, and then the vacuum distillation was preformed to give 4.17 g of yellow 2,2'-methylenebis(1,3-dimethyl-1,3-cyclopentadiene) compound. Yield: 61%.

Example 5

Preparation of [2,2'-methylenebis(1,3-dimethylcyclopentadienyl)zirconium dichloride [Formula XII (R$^1$, R$^2$=CH$_3$; R$^3$, R$^4$=H)]

Two equivalents of n-butyl-lithium were added to a solution in which 3.24 g (16.17 mmol) of 2,2'-methylenebis (1,3-dimethyl-1,3-cyclopentadiene) compound prepared in the example 4 was dissolved in 40 ml of diethyl ether at –78° C. nitrogen atmosphere, and the mixture was reacted for a day with slowly warming to room temperature. The solid filtered under nitrogen atmosphere was washed twice with 20 ml of diethyl ether, and then the solvent was removed completely under reduced pressure. 200 g (0.853 mmol) of lithium salt thus made were dissolved in a mixed solvent containing 15 ml of toluene and 3 ml of tetrahydrofuran. The same equivalent of zirconium tetrachloride compound was added, the mixture was reacted for a day, and then the reactants were filtered, and the solvent of the filtered solution was removed under reduced pressure to give 263 mg of pale yellow solid compound. Yield: 85%.

As described above, the present invention provides a simple method of preparing 1,4,6-substituted, 1,4-substituted, 1,6-substituted, or 1-substituted fulvene compounds.

The method described in the present invention has shorter preparation step and is mass-producible over the method described in prior invention (Korean Patent Application No. 10-2002-51425). Further, the present invention also provides a simple method of preparing an ansa-metallocene compound in which two cyclopentadienyl ligands are bridged by one carbon and there are substituents only at positions adjacent to the bridging point of cyclopentadienyl ligand. Prior art method needed high pressure of carbon monoxide and a temperature higher than 400° C. Prior art method has long reaction steps and must isolate and purify an intermediate by chromatography method, and thus has a problem in mass production. However, the method of the present invention overcomes such a problem and is easily mass-producible.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of preparing a 1,4,6-substituted, 1,4-substituted, 1,6-substituted, or 1-substituted fulvene compound comprising a) reacting Formula I below with a compound of Formula IIa or IIb below to prepare a compound of Formula III below;

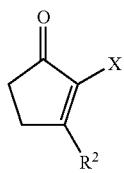
(I)

R$^1$—Li (IIa)

R$^1$—MgX (IIb)

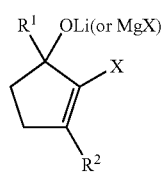
(III)

b) lithiating the compound of the Formula III, and then reacting the resulting lithium salt with an electrophile of Formula IV below to prepare a compound of Formula V below;

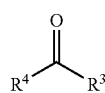
(IV)

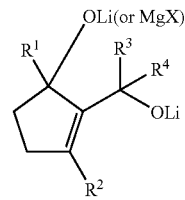
(V)

c) reacting more than one equivalent of the compound of the Formula V with a compound of Formula VI below to prepare an ether, and then dehydrating with an acid catalyst to prepare a compound of Formula VII below; and

R$^5$—Y (VI)

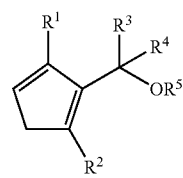
(VII)

d) adding a base to the compound of the Formula VII to prepare a fulvene compound of Formula VIII

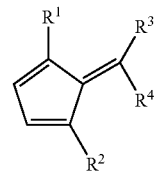

wherein
R$^1$, R$^2$, R$^3$ and R$^4$ are each independently or simultaneously a hydrogen atom; a C$_1$–C$_{20}$ alkyl or aryl comprising optionally an oxygen atom; or a C$_1$–C$_{20}$ alkenyl, alkylaryl or arylalkyl, and
R$^1$ is not a hydrogen atom, and R$^3$ and R$^4$ can be connected together by an alkylidene radical comprising a C$_1$–C$_{20}$ alkyl or aryl radical to form a ring;
X is a halogen atom;
R$^5$ is a C$_1$–C$_{20}$ alkyl, alkenyl, alkylaryl, or a radical of Group XIV metal substituted with an arylalkyl, an aryl, an alkoxyalkyl or a hydrocarbyl;
Y is a leaving group formed by a nucleophilic substitution reaction.

2. A compound of Formula VII below:

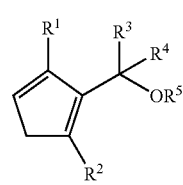
(VII)

wherein
- $R^1$, $R^2$, $R^3$ and $R^4$ are each independently or simultaneously a hydrogen atom; a $C_1$–$C_{20}$ alkyl or aryl comprising optionally an oxygen atom; or a $C_1$–$C_{20}$ alkenyl, alkylaryl or arylalkyl, and
- $R^1$ is not a hydrogen atom, and $R^3$ and $R^4$ can be connected together by an alkylidene radical comprising a $C_1$–$C_{20}$ alkyl or aryl radical to form a ring; and
- $R^5$ is a $C_1$–$C_{20}$ alkyl, alkenyl, alkylaryl, or a radical of Group XIV metal substituted with an arylalkyl, an aryl, an alkoxyalkyl or a hydrocarbyl.

3. A method of preparing the compound of Formula VII below comprising

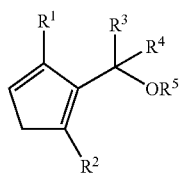
(VII)

a) reacting Formula I below with a compound of Formula IIa or IIb below to prepare a compound of Formula III below;

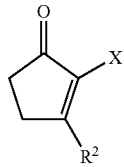
(I)

$R^1$—Li (IIa)

$R^1$—MgX (IIb)

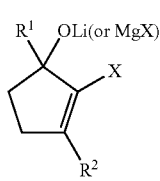
(III)

b) lithiating the compound of the Formula III, and then reacting the resulting lithium salt with an electrophile of Formula IV below to prepare a compound of Formula V below; and

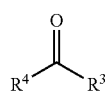
(IV)

-continued

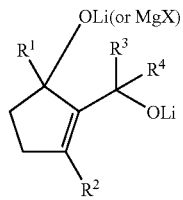
(V)

c) reacting more than one equivalent of the compound of the Formula V with a compound of Formula VI below to prepare an ether, and then dehydrating with an acid catalyst to prepare a compound of the Formula VII $R^5$—Y (VI)

wherein
- $R^1$, $R^2$, $R^3$ and $R^4$ are each independently or simultaneously a hydrogen atom; a $C_1$–$C_{20}$ alkyl or aryl comprising optionally an oxygen atom; or a $C_1$–$C_{20}$ alkenyl, alkylaryl or arylalkyl, and
- $R^1$ is not a hydrogen atom, and $R^3$ and $R^4$ can be connected together by an alkylidene radical comprising a $C_1$–$C_{20}$ alkyl or aryl radical to form a ring;
- X is a halogen atom;
- $R^5$ is a $C_1$–$C_{20}$ alkyl, alkenyl, alkylaryl, or a radical of Group XIV metal substituted with an arylalkyl, an aryl, an alkoxyalkyl or a hydrocarbyl;
- Y is a leaving group formed by a nucleophilic substitution reaction.

4. A method of preparing a fulvene compound of Formula VIII below comprising adding a base to a compound of Formula VII below to prepare the fulvene compound of the Formula VIII:

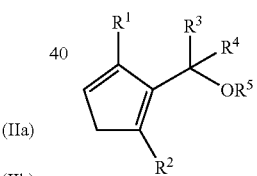
(VII)

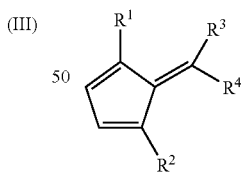
(VIII)

wherein
- $R^1$, $R^2$, $R^3$ and $R^4$ are each independently or simultaneously a hydrogen atom; a $C_1$–$C_{20}$ alkyl or aryl comprising optionally an oxygen atom; or a $C_1$–$C_{20}$ alkenyl, alkylaryl or arylalkyl, and
- $R^1$ is not a hydrogen atom, and $R^3$ and $R^4$ can be connected together by an alkylidene radical comprising a $C_1$–$C_{20}$ alkyl or aryl radical to form a ring; and
- $R^5$ is a $C_1$–$C_{20}$ alkyl, alkenyl, alkylaryl, or a radical of Group XIV metal substituted with an arylalkyl, an aryl, an alkoxyalkyl or a hydrocarbyl.

5. A compound of Formula IX below:

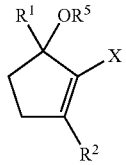
(IX)

wherein

- $R^1$, and $R^2$ are each independently or simultaneously a hydrogen atom; a $C_1$–$C_{20}$ alkyl or aryl comprising optionally an oxygen atom; or a $C_1$–$C_{20}$ alkenyl, alkylaryl or arylalkyl;
- X is a halogen atom; and
- $R^5$ is a $C_1$–$C_{20}$ alkyl, alkenyl, alkylaryl, or a radical of Group XIV metal substituted with an arylalkyl, an aryl, an alkoxyalkyl or a hydrocarbyl.

6. A method of preparing a compound of Formula IX below comprising reacting the compound of the Formula III with a compound of Formula VI below to prepare a compound of the Formula IX:

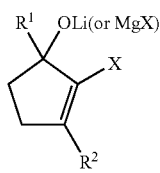
(III)

$R^5$—Y
(VI)

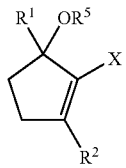
(IX)

wherein

- $R^1$ and $R^2$ are each independently or simultaneously a hydrogen atom; a $C_1$–$C_{20}$ alkyl or aryl comprising optionally an oxygen atom; or a $C_1$–$C_{20}$ alkenyl, alkylaryl or arylalkyl;
- X is a halogen atom;
- $R^5$ is a $C_1$–$C_{20}$ alkyl, alkenyl, alkylaryl, or a radical of Group XIV metal substituted with an arylalkyl, an aryl, an alkoxyalkyl or a hydrocarbyl; and
- Y is a leaving group formed by a nucleophilic substitution reaction.

7. A method of preparing the compound of Formula VII below comprising

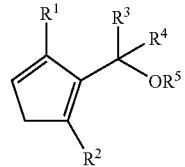
(VII)

a) lithiating the compound of the Formula IX, or converting the compound with a Grignard reagent, and then reacting the resulting organometallic compound with an electrophile of Formula IV below to prepare a compound of Formula X below; and

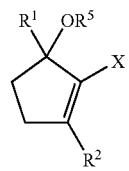
(IX)

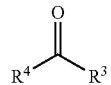
(IV)

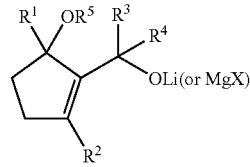
(X)

b) reacting more than one equivalent of the compound of the Formula X with a compound of Formula VI below to prepare an ether, and then dehydrating with an acid catalyst to prepare a compound of the Formula VII $R^5$—Y
(VI)

wherein

- $R^1$, $R^2$, $R^3$ and $R^4$ are each independently or simultaneously a hydrogen atom; a $C_1$–$C_{20}$ alkyl or aryl comprising optionally an oxygen atom; or a $C_1$–$C_{20}$ alkenyl, alkylaryl or arylalkyl, and
- $R^1$ is not a hydrogen atom, and $R^3$ and $R^4$ can be connected together by an alkylidene radical comprising a $C_1$–$C_{20}$ alkyl or aryl radical to form a ring;
- X is a halogen atom;
- $R^5$ is a $C_1$–$C_{20}$ alkyl, alkenyl, alkylaryl, or a radical of Group XIV metal substituted with an arylalkyl, an aryl, an alkoxyalkyl or a hydrocarbyl; and
- Y is a leaving group formed by a nucleophilic substitution reaction.

8. A method of preparing a compound of Formula XI below comprising lithiating the compound of Formula III below or the compound of Formula IX below, or converting the compounds with a Grignard reagent, and then reacting the resulting organometallic the compounds with the compound of the Formula VIII below, and then treating with an acid:

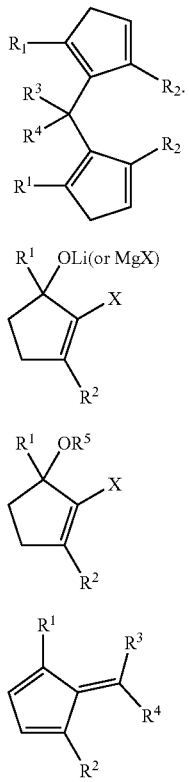

(XI)

(III)

(IX)

(VIII)

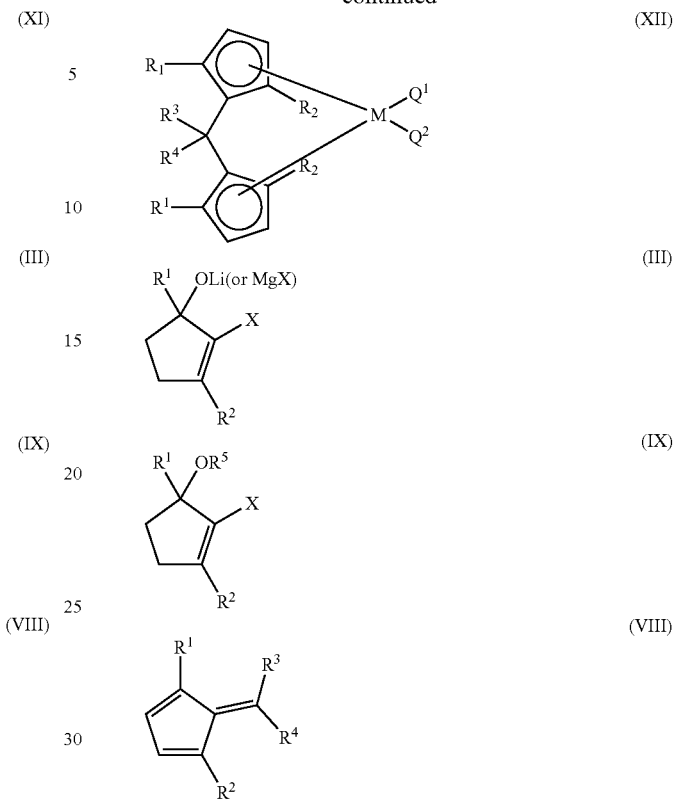

wherein

R$^1$, R$^2$, R$^3$ and R$^4$ are each independently or simultaneously a hydrogen atom; a C$_1$–C$_{20}$ alkyl or aryl comprising optionally an oxygen atom; or a C$_1$–C$_{20}$ alkenyl, alkylaryl or arylalkyl, and R$^1$ is not a hydrogen atom, and R$^3$ and R$^4$ can be connected together by an alkylidene radical comprising a C$_1$–C$_{20}$ alkyl or aryl radical to form a ring;

X is a halogen atom; and

R$^5$ is a C$_1$–C$_{20}$ alkyl, alkenyl, alkylaryl, or a radical of Group XIV metal substituted with an arylalkyl, an aryl, an alkoxyalkyl or a hydrocarbyl.

9. A method of preparing a compound of Formula XII from a compound of Formula XI below, characterized in that the compound of the Formula XI is prepared by reacting a compound of Formula III below or a compound of Formula IX below with lithium metal or converting the compounds with an Grignard reagent, reacting with a compound of Formula VIII below, and then treating with an acid:

(XI)

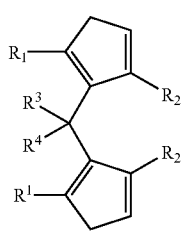

wherein

R$^1$, R$^2$, R$^3$ and R$^4$ are each independently or simultaneously a hydrogen atom; a C$_1$–C$_{20}$ alkyl or aryl comprising optionally an oxygen atom; or a C$_1$–C$_{20}$ alkenyl, alkylaryl or arylalkyl, and R$^1$ is not a hydrogen atom, and R$^3$ and R$^4$ can be connected together by an alkylidene radical comprising a C$_1$–C$_{20}$ alkyl or aryl radical to form a ring;

X is a halogen atom;

R$^5$ is a C$_1$–C$_{20}$ alkyl, alkenyl, alkylaryl, or a radical of Group XIV metal substituted with an arylalkyl, an aryl, an alkoxyalkyl or a hydrocarbyl, Q$^1$ and Q$^2$ are each independently or simultaneously a halogen atom; a C$_1$–C$_{20}$ alkyl, alkenyl, alkylaryl or arylalkyl; an aryl; a substituted or unsubstituted C$_1$–C$_{20}$ alkylidene; a substituted or unsubstituted amido group; a C$_1$–C$_{20}$ alkylalkoxy; or an arylalkoxy; and M is a Group IV metal.

10. The method of claim 1 or 3, wherein the compound of the Formula I is selected from the group consisting of 2-bromo-2-cyclopentene-1-one, 2-bromo-3-methyl-2-cyclopentene-1-one and 2-iodo-3-methyl-2-cyclopentene-1-one.

11. The method of any one of claims 1, 3 or 7, wherein the compound of the Formula IV is selected from the group consisting of acetone, formaldehyde, acetaldehyde, benzaldehyde, benzophenone, methylethylketone, butyraldehyde and propionaldehyde.

12. The method of any one of claims 1, 3, 4, 6, 7, 8 or 9, wherein R$^1$ and R$^2$ are both methyl.

13. The method of any one of claims 1, 3, 4, 7, 8 or 9, wherein R$^1$ and R$^2$ are both methyl, R$^3$ is a hydrogen atom, R$^4$ is a hydrogen atom, methyl or phenyl.

14. The method of any one of claims 1, 3, 6, 7, 8 or 9, wherein $R^1$, $R^2$ and $R^5$ are all methyl, and X is bromine.

15. The method of any one of claims 1, 3, 4, 7, 8 or 9, wherein $R^1$ and $R^2$ are both methyl, $R^3$ and $R^4$ are both hydrogen atom.

16. The method of claims 2 or 5, wherein $R^1$ and $R^2$ are both methyl.

17. The method of claims 2 or 5, wherein $R^1$ and $R^2$ are both methyl, $R^3$ is a hydrogen atom, $R^4$ is a hydrogen atom, methyl or phenyl.

18. The method of claim 2, wherein $R^1$ and $R^2$ are both methyl, $R^3$ and $R^4$ are both hydrogen atoms.

* * * * *